(12) United States Patent
Xu (10) Patent No.: US 11,864,919 B1
(45) Date of Patent: Jan. 9, 2024

(54) CALIBRATING PASSIVE LC SENSOR (71) Applicant: W. L. Gore & Associates, Inc., Newark, DE (US)

(72) Inventor: Minghua Xu, Hockessin, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 129 days.

(21) Appl. No.: 17/678,375

(22) Filed: Feb. 23, 2022

Related U.S. Application Data (62) Division of application No. 15/688,189, filed on Aug. 28, 2017, now Pat. No. 11,284,840.

(60) Provisional application No. 62/380,203, filed on Aug. 26, 2016.

(51) Int. Cl.
*A61B 5/0215* (2006.01)
*A61B 5/00* (2006.01)
*G01R 27/26* (2006.01)
*A61B 5/027* (2006.01)

(52) U.S. Cl.
CPC .......... *A61B 5/6876* (2013.01); *A61B 5/0031* (2013.01); *A61B 5/027* (2013.01); *A61B 5/02152* (2013.01); *A61B 5/02156* (2013.01); *A61B 5/02158* (2013.01); *A61B 5/6862* (2013.01); *G01R 27/26* (2013.01)

(58) Field of Classification Search
CPC ... A61B 5/6876; A61B 5/0031; A61B 5/0215; A61B 5/02152; A61B 5/02156; A61B 5/02158; A61B 5/6862; G01R 27/26
See application file for complete search history.

(56) References Cited

U.S. PATENT DOCUMENTS

| | | |
|---|---|---|
| 3,228,030 A | 1/1966 | Moore |
| 4,206,762 A | 6/1980 | Cosman |
| 5,144,098 A | 9/1992 | Vandeusen |
| 5,480,415 A | 1/1996 | Cox et al. |
| 5,967,986 A | 10/1999 | Cimochowski et al. |
| 6,015,386 A | 1/2000 | Kensey et al. |
| 6,102,862 A | 8/2000 | Grunwald et al. |
| 6,133,797 A | 10/2000 | Lovelace et al. |
| 6,200,268 B1 | 3/2001 | Vince et al. |
| 6,206,835 B1 | 3/2001 | Spillman et al. |
| 6,231,516 B1 | 5/2001 | Keilman et al. |
| 6,254,543 B1 | 7/2001 | Grunwald et al. |
| 6,585,763 B1 | 7/2003 | Keilman et al. |
| 6,855,115 B2 | 2/2005 | Fonseca et al. |
| 7,146,861 B1 | 12/2006 | Cook et al. |
| 7,181,975 B1 | 2/2007 | Bradley et al. |
| 7,191,013 B1 | 3/2007 | Miranda et al. |

(Continued)

FOREIGN PATENT DOCUMENTS

WO 2006/040781 A2 4/2006

*Primary Examiner* — David J. McCrosky (57) ABSTRACT

A flexible, passive pressure sensor includes three LC tank circuits. The first LC tank circuit is a pressure sensing LC tank circuit, having a capacitance that varies in response to changes in environmental pressure. The second and third LC tank circuits are reference LC tank circuits, having capacitances that are relatively constant over changes in environmental pressure. A measurement tool measures the resonant frequencies of the three LC tank circuits and then computes a pressure measurement that accounts for changes in resonant frequencies in the LC tank circuits due to environmental effects and deforming.

5 Claims, 8 Drawing Sheets

(56) References Cited

U.S. PATENT DOCUMENTS

| | | |
|---|---|---|
| 7,245,117 B1 | 7/2007 | Joy et al. |
| 7,399,313 B2 | 7/2008 | Brown et al. |
| 7,452,334 B2 | 11/2008 | Gianchandani et al. |
| 7,568,394 B1 | 8/2009 | Keilman et al. |
| 7,647,831 B2 | 1/2010 | Corcoran et al. |
| 7,677,107 B2 | 3/2010 | Nunez et al. |
| 7,955,268 B2 | 6/2011 | Huelskamp |
| 8,016,875 B2 | 9/2011 | Philipp et al. |
| 8,072,310 B1 | 12/2011 | Everhart |
| 8,187,317 B2 | 5/2012 | Leprince et al. |
| 8,372,139 B2 | 2/2013 | Bailey et al. |
| 8,432,265 B2 | 4/2013 | Rowland et al. |
| 8,493,187 B2 | 7/2013 | Rowland et al. |
| 8,549,923 B2 | 10/2013 | Chommeloux et al. |
| 9,333,365 B2 | 5/2016 | Zhao |
| 2004/0082867 A1 | 4/2004 | Esch et al. |
| 2005/0175665 A1 | 8/2005 | Hunter et al. |
| 2007/0100215 A1 | 5/2007 | Powers et al. |
| 2007/0186677 A1 | 8/2007 | Zunino et al. |
| 2008/0033527 A1 | 2/2008 | Nunez et al. |
| 2008/0077016 A1 | 3/2008 | Sparks et al. |
| 2008/0127739 A1 | 6/2008 | Deangelis et al. |
| 2008/0177131 A1 | 7/2008 | Dancu |
| 2009/0030291 A1 | 1/2009 | O'Brien et al. |
| 2009/0105557 A1 | 4/2009 | Najafi et al. |
| 2010/0058583 A1 | 3/2010 | Cros et al. |
| 2010/0107770 A1 | 5/2010 | Serban et al. |
| 2011/0120228 A1 | 5/2011 | Main et al. |
| 2011/0257491 A1 | 10/2011 | Robertson et al. |
| 2012/0029323 A1 | 2/2012 | Zhao |
| 2013/0148255 A1 | 6/2013 | Taylor et al. |
| 2013/0165801 A1 | 6/2013 | Min |
| 2013/0197336 A1 | 8/2013 | Flo et al. |
| 2014/0080409 A1 | 3/2014 | Frankland et al. |
| 2014/0128687 A1 | 5/2014 | White et al. |
| 2014/0273824 A1 | 9/2014 | Fenner et al. |
| 2014/0296687 A1 | 10/2014 | Irazoqui et al. |
| 2014/0306807 A1 | 10/2014 | Rowland et al. |
| 2014/0350348 A1 | 11/2014 | Tee et al. |
| 2014/0364714 A1 | 12/2014 | Ameri et al. |
| 2015/0177077 A1 | 6/2015 | Hanson et al. |
| 2015/0196225 A1 | 7/2015 | Rusu et al. |
| 2016/0022447 A1* | 1/2016 | Kim ............... A61B 5/0215 623/1.15 |
| 2016/0029956 A1 | 2/2016 | Rowland et al. |
| 2016/0231098 A1 | 8/2016 | Otaka et al. |
| 2017/0364905 A1 | 12/2017 | Hart |
| 2019/0131969 A1 | 5/2019 | Boese et al. |
| 2019/0137322 A1 | 5/2019 | Choi et al. |

\* cited by examiner

CALIBRATING PASSIVE LC SENSOR

RELATED APPLICATIONS

This application is a divisional of U.S. application Ser. No. 15/688,189, filed Aug. 28, 2017, and titled CALIBRATING PASSIVE LC SENSOR, which claims priority to U.S. Provisional Application No. 62/380,203, filed Aug. 26, 2016, and titled CALIBRATING PASSIVE LC SENSOR. The contents of those applications (including the Appendix) are incorporated herein by reference for all purposes.

FIELD

Embodiments of the present disclosure generally relate to improved passive LC sensors for medical devices. More specifically, embodiments of the present disclosure relate to sensors and techniques for more precisely measuring and monitoring pressure within a blood vessel.

BACKGROUND

Measuring blood pressure is an important diagnostic tool in many medical treatments, especially when treating vascular maladies. For example, aneurysms are often treated by implanting a stent-graft within the aneurysm pocket. Monitoring blood pressure at the stent-graft can be important in tracking patient health and treatment effectiveness. Various pressure sensors have been proposed for monitoring blood pressure within a vessel, including capacitive pressure sensors. Among them, thin flexible inductive-capacitive (LC) pressure sensors have great potential to integrate within a graft or stent. However, these LC sensors may have significant variances caused by interactions with surrounding tissue and/or variances caused by deforming circuit components.

SUMMARY

Embodiments of the present disclosure provide improved measurement correction techniques and an improved passive sensor by integrating two or more reference LC tank circuits, which can compensate for environmental tissue dielectric effects and/or the effects caused physical bending and deforming on the sensor's measurements.

According to one example, a passive inductor-capacitor pressure sensor includes three LC tank circuits. The first LC tank circuit is a pressure sensing LC tank circuit, having a capacitance that varies in response to changes in environmental pressure and a resonant frequency that depends on the inductance and the capacitance of the LC tank circuit. The second and third LC tank circuits are reference LC tank circuits, having capacitances that are relatively constant over changes in environmental pressure, for example, less than 0.05% change from 500 mm Hg to 1000 mm Hg (from high altitude to below sea level) and resonant frequencies that depend on the inductances and the capacitances of those LC tank circuits.

In one variant of that example, the first LC tank circuit is located between the second and third LC tank circuits. In another variant of that example, the first LC tank circuit is located at one end of the passive inductor-capacitor pressure sensor. In a third variant, the three LC tank circuits are placed in close proximity to each other so that the interactions with the environment and the bending and/or deforming components are approximately equal across all three LC tank circuits. In one variant of that example, the pressure sensitive LC tank circuit includes a pressure sensitive dielectric medium or a hermetically sealed cavity for pressure sensing.

In another variant of that example, the second and third LC tank circuits have inductive coil structures and capacitive structures substantially similar or identical to that of the first LC tank circuit, though with two different pressure insensitive dielectric media, so that dielectric properties of the surrounding media or tissue induce an equivalent parasitic capacitance to all the LC tank circuits and so that mechanical deformation of the inductive coil structures induces an equivalent inductance change to all the LC tank circuits, with the three LC tank circuits having different resonant frequencies that are separated enough to be distinguished by an external sensor reader.

In another example, a method for compensating for shifts in resonant frequency due to dielectric properties of a surrounding medium and non-pressure related mechanical deformation in an inductor-capacitor pressure sensor includes: measuring the resonant frequency of a pressure-sensing LC tank circuit; measuring the resonant frequency of a first reference LC tank circuit; and measuring the resonant frequency of a second reference LC tank circuit. This exemplary method further includes determining a corrected capacitance of the pressure-sensing LC tank circuit utilizing the resonant frequencies of the first and second reference LC tank circuits using the following equation:

$$C_{1V} = \frac{m_1 - m_2}{m_3 - m_2}(C_3 - C_2) + C_2$$

where $C_{1V}$ is the corrected capacitance, $C_2$ is the capacitance of the first reference LC tank circuit, and $C_3$ is the capacitance of the second reference LC tank circuit. In that equation, $m_1$ is defined as $$\left(\frac{1}{2\pi f_1}\right)^2$$

(where $f_1$ is the resonant frequency of the pressure-sensing LC tank circuit), $m_2$ is defined as $$\left(\frac{1}{2\pi f_2}\right)^2$$

(where $f_2$ is the resonant frequency of the first reference LC tank circuit), and $m_3$ is defined as $$\left(\frac{1}{2\pi f_3}\right)^2$$

(where $f_3$ is the resonant frequency of the second reference LC tank circuit).

This exemplary method further includes determining a corrected pressure (P) from the corrected $C_{1V}$ calculation based on the relationship between $C_{1V}$ and P.

In one variant of that example, the pressure-sensing LC tank circuit is positioned between the first and second reference LC tank circuits. In another variant of that example, the pressure-sensing LC tank circuit is located at one end of the passive inductor-capacitor pressure sensor.

In one variant of that example, determining the corrected capacitance of the pressure-sensing LC tank circuit includes accounting for changes in resonant frequencies caused by environmental dielectric properties and/or mechanical deformation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
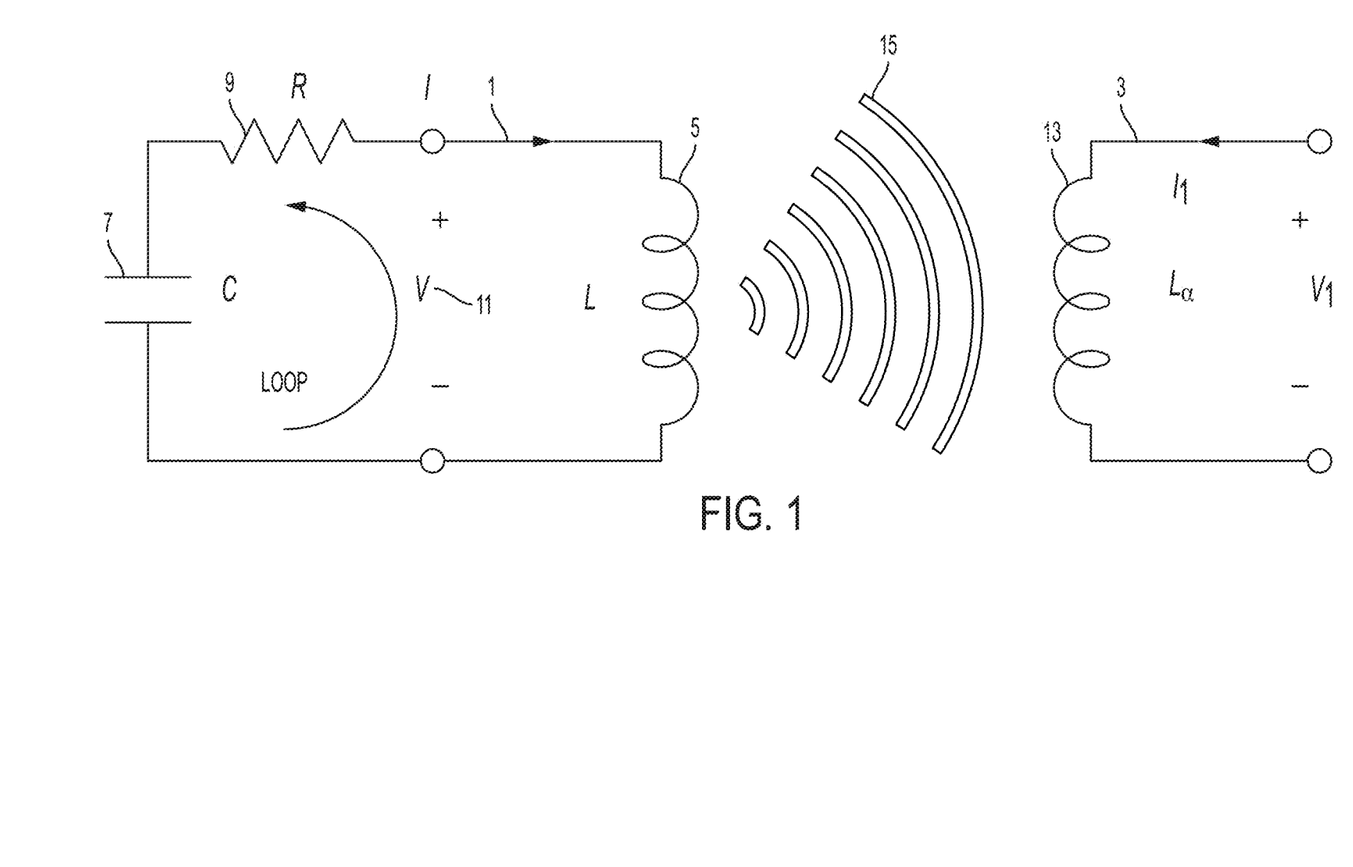
FIG. 1 illustrates a diagram of an exemplary LC tank circuit and a portion of an exemplary circuit for a sensor reader, according to embodiments of the present disclosure.

According to some embodiments, FIG. 1 shows an electrical equivalent resonant circuit 1 of a passive LC sensor with an equivalent capacitor C (reference number 7) and inductor L (reference number 5), and an equivalent electrical circuit 3 of a sensor reader, where the reader antenna 13 wirelessly measures the resonant frequency of circuit 1 by magnetic induction between the sensor antenna (e.g., the inductor 5) and reader antenna 13. The electrical equivalent resonant circuit 1 can also be referred to as an LC circuit, LC tank, or LC tank circuit, because of the voltage 11 that it can hold. The LC tank 1 has a resonant frequency that depends on the inductance and capacitance provided by the inductor 5 and capacitor 7, respectively. If the capacitor 7 is configured to vary its capacitance in response to a change in external pressure, the LC tank circuit can serve as a pressure sensor. As one of skill in the art will readily appreciate, there are a wide variety of electrical components that exhibit capacitive and inductive characteristics and that can be used in various embodiments discussed herein. As also shown in FIG. 1, the LC tank circuit 1 also includes an equivalent resistor 9 that represents energy loss due to RF absorption.

In general, a smaller resistance is required to provide a higher quality factor (Q, e.g., greater than 35) so that the ring-down signal 15 from the sensor can last long enough for the reader to pick up the resonance signal.

One of the benefits of an LC tank (e.g., LC tank 1 in FIG. 1) is that characteristics of that circuit (e.g., resonant frequency) can be determined without needing to include a power source, such as a battery, as part of the circuit. Instead, a reader or monitoring tool (e.g., equivalent electrical circuit 3 in FIG. 1) can interact wirelessly with that circuit to detect those characteristics of the LC tank 1. Another benefit of an LC tank (e.g., LC tank 50 or 60 in FIGS. 3-4) is that the LC circuit can be formed from a thin-flexible structure, such that the LC sensor can be integrated within a stent-graft to measure pressure at a site without blocking blood flow through the vessel. These advantages render the LC tank as a suitable candidate for a pressure sensor for monitoring blood pressure within a vessel.

For example, if a dielectric material that reacts to external pressure is placed within the capacitor (e.g., capacitor 7 in FIG. 1), a change in blood pressure will cause a change in capacitance in the LC tank, which results in a change in its resonant frequency. For another example, the LC tank may be set up so that the plates of the capacitor 7 move in response to external pressures, which will affect the capacitance and the resonant frequency of the LC tank. Under either approach, if the other characteristics of the LC tank (e.g., inductance) remain relatively constant, the change in the resonant frequency can be used to determine the change in capacitance, which can then be used to determine a measurement of the blood pressure within the vessel.

Figure 2:
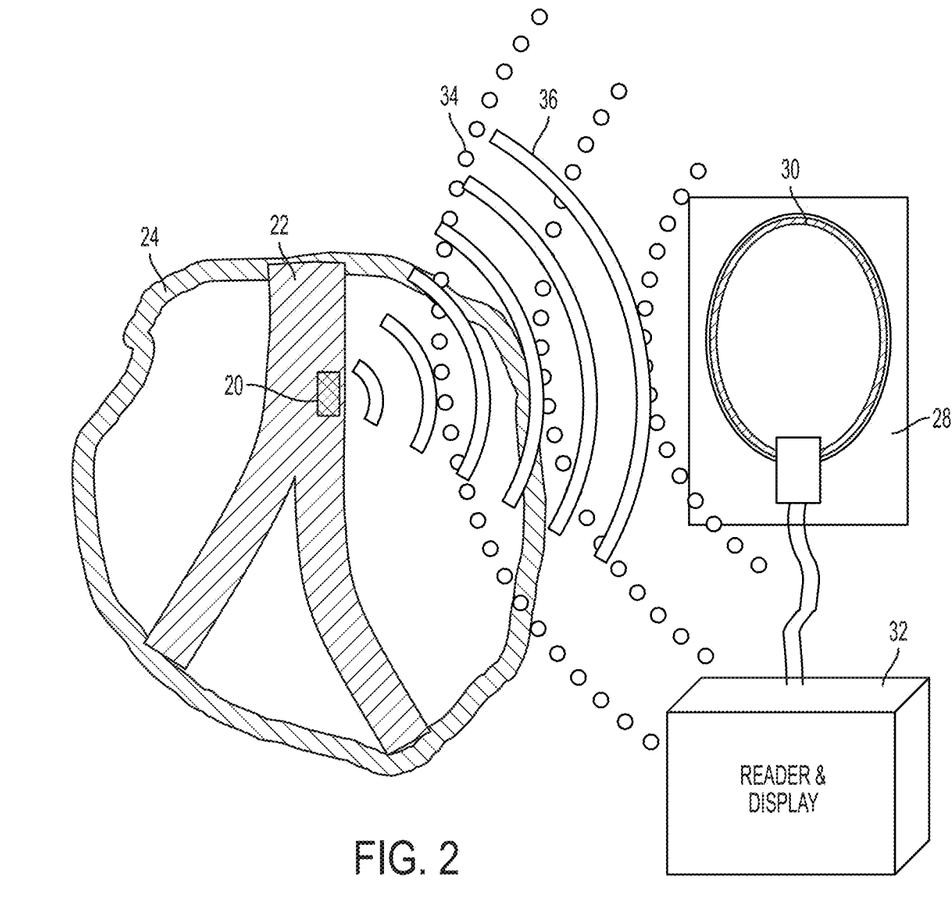
FIG. 2 illustrates an exemplary pressure sensor coupled to a stent-graft as well as an exemplary measuring tool, according to embodiments of the present disclosure.

These approaches can be seen in FIG. 2, in which a pressure sensor 20 uses an LC circuit to monitor blood pressure at a stent-graft 22 placed to treat an aneurism in the body 24. In various embodiments, the pressure sensor may be placed on an outer surface of the stent-graft, an inner surface of the stent-graft, or may be integrated within the stent-graft. Thus, measuring blood pressure at the stent-graft includes measuring blood pressure outside of the stent-graft and/or within the stent-graft. The measurement device 28 includes an antenna 30 and a reader/display 32. The reader/display 32 can include a processor, memory, and other hardware and/or software needed to measure signals from the antenna 30 and process those signals to determine (and perhaps display) the blood pressure measurements. The measuring device 28 emits a pulse 34, which causes the pressure sensor to emit a ring-down signal 36. The measuring device 28 analyzes the ring-down signal 36 to identify pressure within the stent-graft 22. Additional details regarding these processing steps are provided below.

In some embodiments, the antenna 30 emits RF signals 34 at a variety of frequencies at different times and measures when the pressure sensor 20 absorbs those frequencies. In other embodiments, the antenna 30 emits energy at a variety of frequencies simultaneously and then detects energy 36 emitted from the LC circuit within the pressure sensor 20, which will indicate the resonant frequency of the LC circuit. As discussed above, measurements of the resonant frequency can be used to determine blood pressure at the pressure sensor.

At the same time, the accuracy of blood pressure measurements with thin flexible LC sensors is limited by several factors that can also affect the resonant frequency. For example, tissues surrounding the pressure sensor can have a dielectric effect on the LC circuit's antenna coil, which adds a parasitic capacitance into the LC circuit. Because of the tight restrictions on size for these pressure sensors, any protective layers added to the LC circuit may often be thin, such that the ability to shield the LC circuit from the surrounding media may be limited. Thus, accounting for the effect of the surrounding tissue on the capacitance of the LC circuit can improve the accuracy of the blood pressure measurement.

Figure 3:
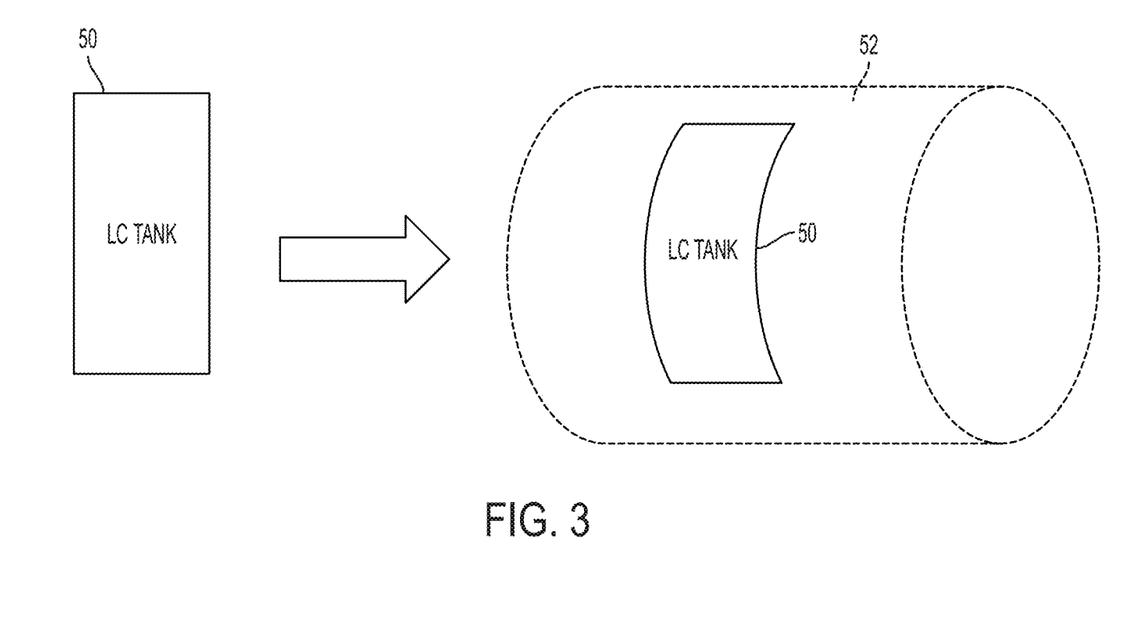
FIG. 3 illustrates an exemplary pressure sensor having an LC tank circuit with a planar antenna and said pressure sensor coupled to a stent-graft, according to embodiments of the present disclosure.
Figure 4:
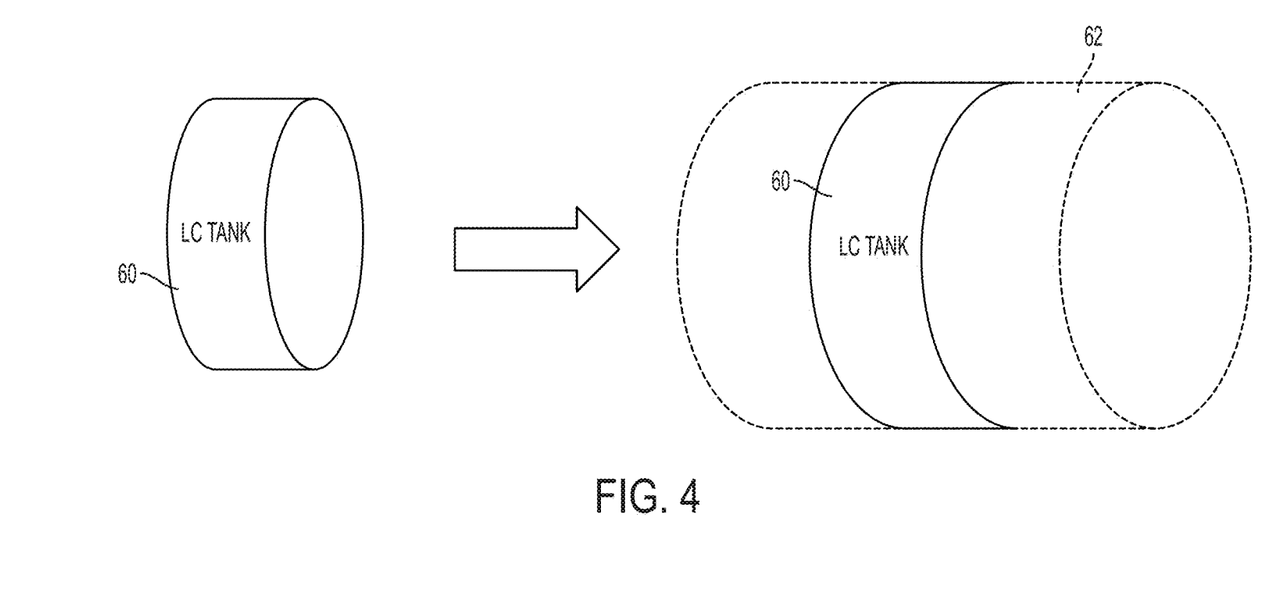
FIG. 4 illustrates an exemplary pressure sensor having an LC tank circuit with a cylindrical antenna and that pressure sensor coupled to a stent-graft, according to embodiments of the present disclosure.

The accuracy of the blood pressure measurement may also be affected by changes to the inductance of the LC circuit's antenna coil (e.g., inductor 5 in FIG. 1). Referring now to FIG. 3, an LC tank 50 can be built with a planar antenna. However, to conform to the non-planar shape of a stent-graft 52, LC tank 50 is bent into a corresponding profile. This can change the shape and inductance of the inductor 5. This effect can be somewhat mitigated by using a cylindrical antenna, as shown with the LC tank 60 and the stent-graft 62 in FIG. 6. However, there will typically be additional changes in inductance as the LC tank 60 is secured to the stent-graft 62. Furthermore, after insertion the LC tank 50, 60 will frequently and repeatedly bend and change shape in response to the pulsating blood flow in the vessel caused by heartbeats. Thus, these factors cause blood pressure measurements taken using a single flexible LC tank to be less accurate.

In some embodiments, a pressure sensor is formed using multiple LC tanks to improve the accuracy of the blood pressure measurements. This pressure sensor provides many of the characteristics important for implantation within a blood vessel, since it is foldable, transmits wirelessly, and does not require internal power (e.g., a battery). In addition, as discussed below, this sensor enables more precise blood pressure measurements within the vessel.

Figure 5:
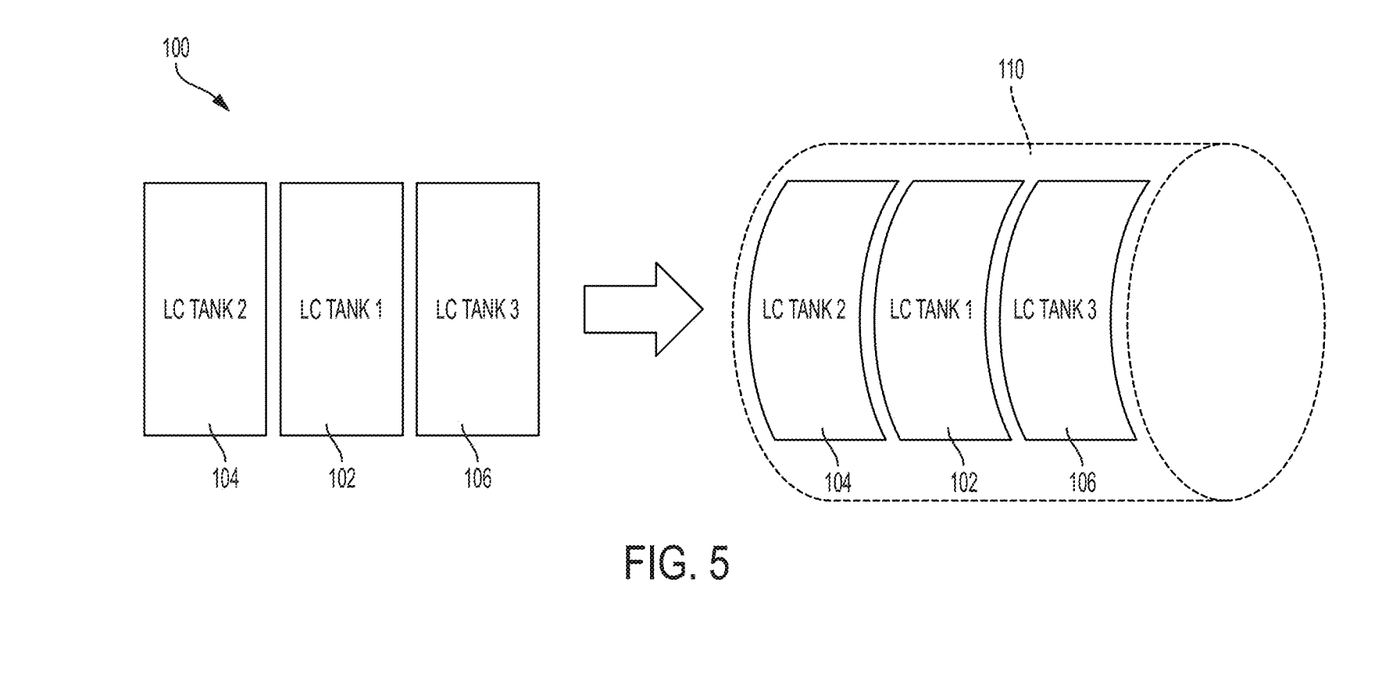
FIG. 5 illustrates a pressure sensor having three exemplary LC tank circuits with planar antennas and said pressure sensor coupled to a stent-graft, according to embodiments of the present disclosure.

Referring to FIG. 5, a pressure sensor 100 includes three LC tanks 102-106, formed with planar antennas, coupled to a stent-graft 110. The first LC tank 102 is pressure sensitive, meaning that its resonant frequency changes in response to changes in pressure. This can be accomplished, for example, by including an elastic dielectric material within the capacitor 7. The other two LC tanks 104, 106 are not pressure sensitive, meaning that their resonant frequencies are relatively unaffected by changes in pressure. However, all three LC tanks are responsive to physical bending as well as environmental tissue dielectric effect (and other non-pressure factors affecting the resonant frequency). Thus, the other two LC tanks 104, 106 serve as reference LC tanks that sense tissue dielectric effects and bending and deforming effects that also occur on the first LC tank 102.

As also shown in FIG. 5, these three LC tanks 102-106 are secured to the stent-graft 110 in close proximity to each other, for example, separated by a gap of approximately 2-5 millimeters. As a result, factors affecting inductance and factors affecting capacitance (other than pressure) will be the same or substantially similar across the three LC tanks (102-106).

Figure 6:
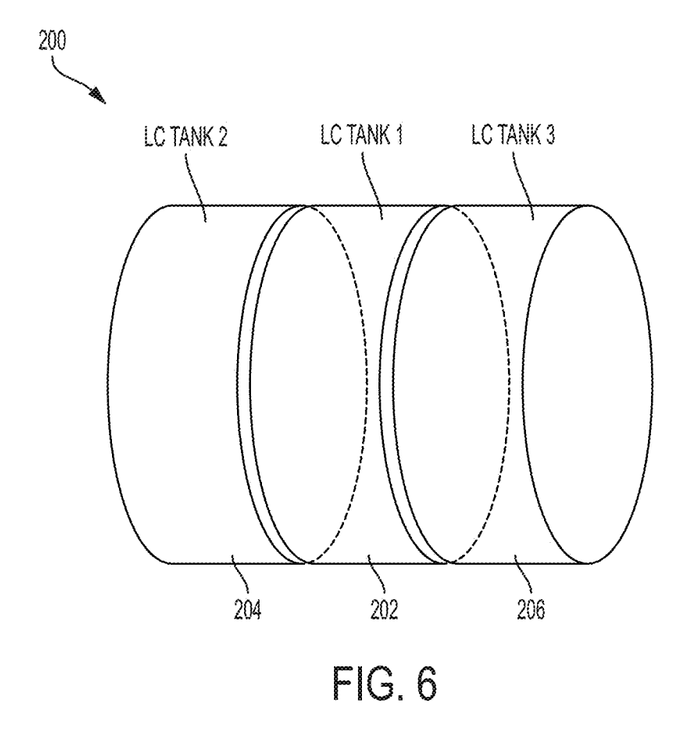
FIG. 6 illustrates a pressure sensor having three exemplary LC tank circuits with cylindrical antennas, according to embodiments of the present disclosure.

FIG. 6 illustrates a pressure sensor 200 with three LC tanks 202-206 formed with cylindrical antennas. FIG. 6 further shows their relative positioning as if they were coupled to a stent-graft. The first LC tank 202 is pressure sensitive, meaning that its resonant frequency changes in response to changes in pressure. This can be accomplished, for example, by including an elastic dielectric material or vacuum cavity within the capacitor 7. The other two LC tanks 204, 206 are not pressure sensitive, meaning that their resonant frequencies are unaffected by changes in pressure. However, all three LC tanks will be responsive to physical changes as well as environmental tissue dielectric effect (and other non-pressure factors affecting the resonant frequency). Thus, the other two LC tanks 204, 206 serve as reference LC tanks that sense tissue dielectric effects and bending and deforming effects that also occur on the first LC tank 202.

In other words, in both FIGS. 5 and 6, the first LC tank (102, 202) uses a variable or pressure-sensitive capacitor whose capacitance ($C_{1V}$) changes in response to changes in environmental pressures (e.g., changes in blood pressure). The other two LC tanks (104, 106, 204, 206) have capacitors whose capacitance ($C_2$, $C_3$, respectively) do not change in response to changes in environmental pressures. These three capacitors may be configured with different dielectric media to have three different capacitance values such that the three LC tanks have different resonant frequencies that can be readily distinguished by an external reader. With these additional reference measurements, the measurements of the first LC tank (102, 202) can be corrected to account for tissue dielectric effects as well as bending and deforming effects using the measurements of the other two LC tanks (104, 106, 204, 206).

In addition, these three LC tanks are constructed to have equivalent or substantially equivalent inductance (L), and experience equivalent or substantially equivalent parasite capacitance ($C_{par}$) and equivalent or substantially equivalent substrate and environmental capacitance and loss ($C_{sub}$). For example, in some embodiments all three LC tanks have similar inductive coils or even substantially identical inductive coils. As a result, any bending of the pressure sensor causes equivalent or substantially equivalent inductance change ($\Delta L$) in all three LC tanks.

A measurement device (e.g., measurement device 28 in FIG. 2) can measure the resonant frequencies of the three LC tanks (102-106 or 202-206), and can process those measured frequencies in a manner that accounts for changes in inductance and changes in capacitance due to factors other than pressure. The three capacitors $C_1$, $C_2$, and $C_3$ have different capacitance values, so that the corresponding resonant frequencies of three LC tanks are different enough to be distinguished. Additional details regarding these processing steps are provided below. Thus, using a pressure sensor with these three LC tank circuits and using these processing steps improves the precision of blood pressure measurements.

In an LC circuit, the resonant frequency (f) is:

$$f = 1/(2\pi\sqrt{LC}) \quad \text{(Eq. 1)}$$

where L is the inductance of the LC circuit and C is the capacitance of the LC circuit. For simplicity, Equation 1 may be rewritten in terms of a measurement "m":

$$m = \left(\frac{1}{2\pi f}\right)^2 = LC \quad \text{(Eq. 2)}$$

The resonant frequencies of the three LC tanks are measured, resulting in measurements $m_1$, $m_2$, and $m_3$, which relate as follows:

$$m_1 = \left(\frac{1}{2\pi f_1}\right)^2 = (L + \Delta L)(C_{1V} + C_{par} + C_{sub}) \quad \text{(Eq. 3)}$$

$$m_2 = \left(\frac{1}{2\pi f_2}\right)^2 = (L + \Delta L)(C_2 + C_{par} + C_{sub}) \quad \text{(Eq. 4)}$$

$$m_3 = \left(\frac{1}{2\pi f_3}\right)^2 = (L + \Delta L)(C_3 + C_{par} + C_{sub}) \quad \text{(Eq. 5)}$$

In other words, using the three LC tanks in this manner provides three measurement ($m_1$, $m_2$ and $m_3$) and equations with three unknowns ($C_{1V}$, $C_{par}+C_{sub}$ and $\Delta L$).

These equations can be manipulated so that two of the three unknown factors ($C_{par}+C_{sub}$ and $\Delta L$) cancel out. First, two of the equations are subtracted as shown below:

$$m_3 - m_2 = (L + \Delta L)(C_3 - C_2) \quad \text{(Eq. 6)}$$

$$m_1 - m_2 = (L + \Delta L)(C_{1V} - C_2) \quad \text{(Eq. 7)}$$

Then a ratio of these equations are taken:

$$\frac{m_1 - m_2}{m_3 - m_2} = \frac{C_{1V} - C_2}{C_3 - C_2} \quad \text{(Eq. 8)}$$

Solving this equation for $C_{1V}$ results in the following equation:

$$C_{1V} = \frac{m_1 - m_2}{m_3 - m_2}(C_3 - C_2) + C_2 \quad \text{(Eq. 9)}$$

In this equation, $C_{1V}$ and $m_1$ are functions of environmental pressure (P), while $m_2$, $m_3$, $C_2$ and $C_3$ are independent and will not change with pressure P.

Using the term $P_0$ to refer to an initial environmental pressure, a change in capacitance ($\Delta C_V$) can then be used to determine a change in the environmental pressure ($\Delta P$). First, we can break up $C_{1V}$ into two parts:

$$C_{1V} = C_{1V}\{P\} = C_{1V}\{P_0 + \Delta P\} = C_{10}\{P_0\} + \Delta C_V\{\Delta P\} \quad \text{(Eq. 10)}$$

where brackets are used to indicate that capacitance (e.g., $C_{1V}$) is a function of pressure (e.g., P).

Combining Equation 9 and Equation 10 results in the following equation:

$$\frac{m_1\{P_0 + \Delta P\} - m_2}{m_3 - m_2}(C_3 - C_2) = C_{10}\{P_0\} + \Delta C_V\{\Delta P\} - C_2 \quad \text{(Eq. 11)}$$

If measurements are taken of the three LC tanks at the initial pressure $P_0$ (i.e., with $\Delta P=0$, $\Delta C_V\{0\}=0$) those measurement can be referred to as $m^*_2$, $m^*_1(P_0)$, and $m^*_3$, and Equation 11 reduces to:

$$C_{10}\{P_0\} - C_2 = \frac{m_1^*(P_0) - m_2^*}{m_3^* - m_2^*}(C_3 - C_2) \quad \text{(Eq. 12)}$$

Using Equation 11, Equation 12 can be rewritten as:

$$\Delta C_V\{\Delta P\} = \left(\frac{m_1\{P_0 + \Delta P\} - m_2}{m_3 - m_2} - \frac{m_1^*(P_0) - m_2^*}{m_3^* - m_2^*}\right)(C_3 - C_2) \quad \text{(Eq. 13)}$$

These equations can be further simplified by combining some of the terms into new variables, as follows:

$$R_m^*(P_0) = \frac{m_1^*\{P_0\} - m_2^*}{m_3^* - m_2^*} \quad \text{(Eq. 14)}$$

$$R_m(P_0 + \Delta P) = \frac{m_1\{P_0 + \Delta P\} - m_2}{m_3 - m_2} \quad \text{(Eq. 15)}$$

$$C_{ref} = C_3 - C_2 \quad \text{(Eq. 16)}$$

Using these variables, the earlier equations simplify to:

$$\Delta C_V\{\Delta P\} = C_{ref}(R_m\{P_0 + \Delta P\} - R_m^*\{P_0\}) \quad \text{(Eq. 17)}$$

In sum, by using this approach, the relationship between $\Delta C_V$ and $\Delta P$ is independent from $C_{par}+C_{sub}$ as well as $\Delta L$. Consequently, a controlled calibration measurement can be used to derive a curve of $\Delta P$ (relative to $P_0$) vs. $\Delta C_V$. For example, during one exemplary calibration technique, a sensor with three LC tanks, which may be built into a graft, is placed into an air chamber in which the air pressure is measured by a calibrated standard pressure sensor. A set of pressures, including the initial pressure $P_0$, is set in the air chamber. At each pressure setting, the resonant frequencies of the three LC tanks are wirelessly detected. Then, using Eq. 17, a calibration curve of $\Delta P$ (relative to $P_0$) vs. $\Delta C_V$ is computed from the above measurements. As discussed above, this calibration curve is independent from both the surrounding tissue dielectric effect and the deforming/bending effect. Therefore, only a single calibration for multiple LC tanks as described above is needed. This calibration curve of $\Delta P$ (relative to $P_0$) vs. $\Delta C_V$ is used to identify changes in blood pressure when the device is implanted.

In addition, the pressure sensor might not be around $P_0$ when the device is implanted. To get to the base point $R^*_m\{P_0\}$, an on-site calibration measurement with other means is performed, for example, using a pressure catheter to measure the blood pressure at the site. The previously-derived calibration curve for this sensor will then indicate any pressure change $\Delta P$ from the capacitance change $\Delta C_V$, calculated from the measured resonant frequencies.

Figure 7:
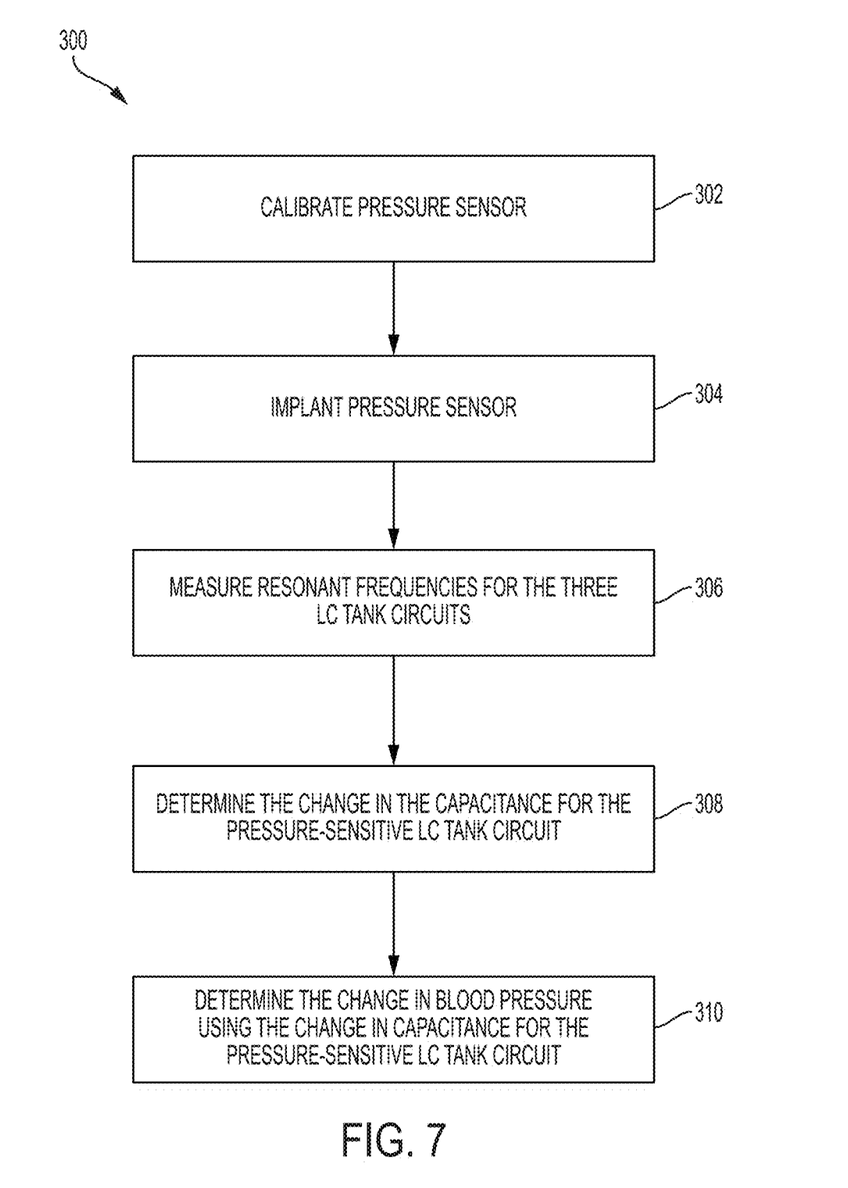
FIG. 7 illustrates steps for measuring blood pressure within a vessel using a pressure sensor with three LC tank circuits, according to embodiments of the present disclosure.

An exemplary method 300 for determining blood pressure using a pressure sensor is shown in FIG. 7. As shown in block 302, the method begins with calibrating the pressure sensor. This includes creating a calibration curve for the pressure sensor (e.g., $\Delta P$ (relative to $P_0$) vs. $\Delta C_V$) by measuring the resonant frequencies of the three LC tanks at a set of known pressures. As shown in block 304, the pressure sensor is implanted in the patient. In this step, the flexibility of the LC pressure sensor may facilitate easy implantation. For example, the pressure sensor may be coupled to a stent-graft in its expanded state. The stent-graft and pressure sensor may be then crushed and/or folded for insertion and subsequent expansion at the tissue site. In other cases, the LC pressure sensor may be built into an arteriovenous (AV) graft which may be surgically implanted into human body. As shown in block 306, the resonant frequencies of the three LC tank circuits are measured wirelessly by an external reader. Using those measurements, the change in capacitance for the pressure-sensitive LC tank circuit is determined, using the equations and techniques discussed above, as shown in block 308. Finally, as shown in block 310, the change in blood pressure is determined using the change in capacitance for the pressure-sensitive LC tank circuit.

In some embodiments, blocks 306, 308, and 310 are performed by a measurement device (e.g., 28 in FIG. 2). For example, these steps could be automatically performed, in whole or in part, by a processor executing instructions stored in a tangible, non-transitory storage medium, without user interaction. These instructions cause the processor to implement the equations and techniques discussed above.

In some embodiments, methods for using a pressure sensor (e.g., a pressure sensor with three LC tanks) includes crushing and/or folding the pressure sensor for insertion into a patient's body. The flexible nature of the LC circuits enable the pressure sensor to expand with the graft stent without degrading.

Figure 8:
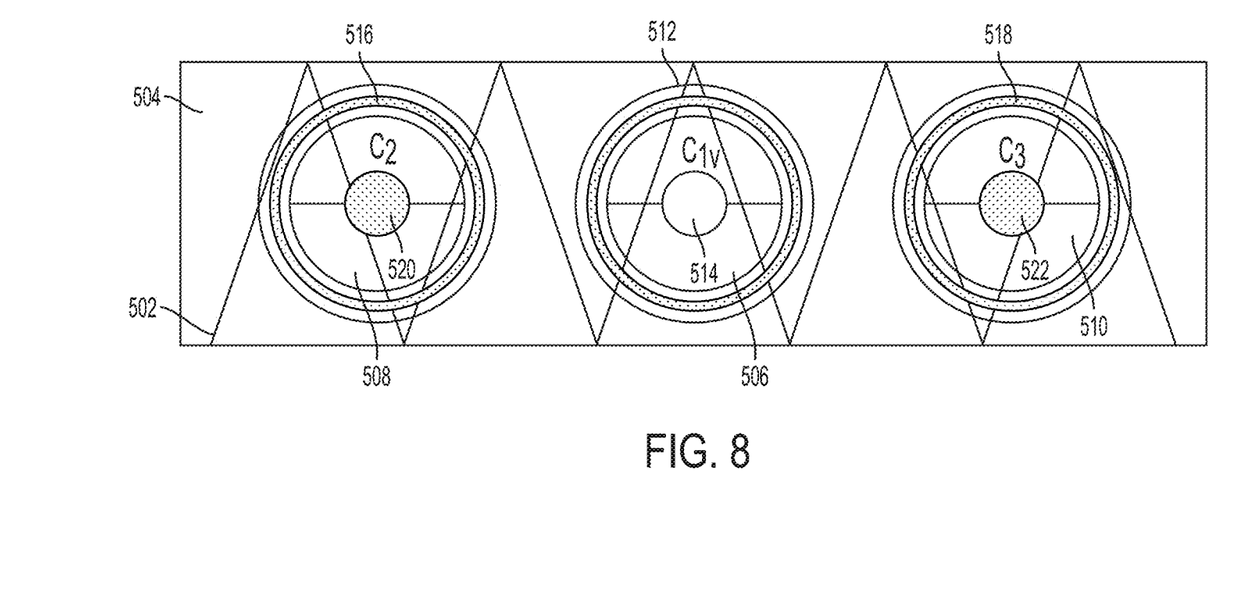
FIG. 8 illustrates a portion of a stent graft to which a pressure sensor is coupled and depicts components of three LC tank circuits that form the pressure sensor, according to embodiments of the present disclosure.

Referring now to FIG. 8, a stent-graft 500 includes a stent 502 and a graft 504. Coupled to the graft 504 are three LC circuits 506, 508, 510. In other embodiments, those circuits are coupled to the stent 502. LC circuit 506 includes an inductor 512 and a variable, pressure sensitive capacitor 514 whose capacitance ($C_{1V}$) changes in response to external pressures. LC circuits 508, 510 include inductors 516, 518 and capacitors 520, 522 whose capacitances do not change in response to external pressures.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A method for compensating for shifts in resonant frequency due to dielectric properties of a surrounding medium and non-pressure related mechanical deformations in an inductor-capacitor pressure sensor located in a circulatory vessel, the method comprising:
   measuring the resonant frequency of a pressure-sensing LC tank circuit while the pressure-sensing LC tank circuit is within a circulatory vessel;
   measuring the resonant frequency of a first reference LC tank circuit while the first reference LC tank circuit is within the circulatory vessel;
   measuring the resonant frequency of a second reference LC tank circuit while the second reference LC tank circuit is within the circulatory vessel; and
   determining a corrected capacitance of the pressure-sensing LC tank circuit utilizing the resonant frequencies of the first and second reference LC tank circuits using the equation:

$$C_{1V} = \frac{m_1 - m_2}{m_3 - m_2}(C_3 - C_2) + C_2$$

wherein $C_{1V}$ is a corrected capacitance of the pressure-sensing LC tank circuit, $C_2$ is the capacitance of the first reference LC tank circuit, and $C_3$ is the capacitance of the second reference LC tank circuit; and 2 wherein $m_1$ is defined as $$\left(\frac{1}{2\pi f_1}\right)^2$$

with $f_1$ being the resonant frequency of the pressure-sensing LC tank circuit, $m_2$ is defined as $$\left(\frac{1}{2\pi f_2}\right)^2$$

with $f_2$ being the resonant frequency of the first reference LC tank circuit, and $m_3$ is defined as $$\left(\frac{1}{2\pi f_3}\right)^2$$

with $f_3$ being the resonant frequency of the second reference LC tank circuit.

2. The method of claim 1 further comprising a step of determining a corrected pressure from the corrected capacitance based on a relationship between $C_{1V}$ and the corrected pressure.

3. The method of claim 1, wherein the pressure-sensing LC tank circuit is positioned between the first and second reference LC tank circuits.

4. The method of claim 1, wherein the pressure-sensing LC tank circuit is located at one end of the inductor-capacitor pressure sensor.

5. The method of claim 1, wherein determining the corrected capacitance of the pressure-sensing LC tank circuit includes accounting for changes in the resonant frequencies caused by environmental dielectric properties and/or mechanical deformation.

* * * * *